(12) United States Patent
Hallinan et al.

(10) Patent No.: US 8,742,168 B2
(45) Date of Patent: Jun. 3, 2014

(54) PROCESS FOR THE PRODUCTION OF ACETIC ACID

(75) Inventors: Noel C. Hallinan, Loveland, OH (US); Brian Salisbury, Oxford, PA (US); Wayne Joseph Brtko, Glen Mills, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 571 days.

(21) Appl. No.: 13/149,538

(22) Filed: May 31, 2011

(65) Prior Publication Data

US 2012/0310009 A1 Dec. 6, 2012

(51) Int. Cl.
*C07C 51/12* (2006.01)

(52) U.S. Cl.
USPC ......................................................... 562/519

(58) Field of Classification Search
None
See application file for complete search history.

(56) References Cited

U.S. PATENT DOCUMENTS

| | | | |
|---|---|---|---|
| 5,416,237 A | 5/1995 | Aubigne et al. | |
| 5,442,107 A * | 8/1995 | Beevor et al. ................. | 562/519 |
| 5,817,869 A | 10/1998 | Hinnenkamp et al. | |
| 5,932,764 A | 8/1999 | Morris et al. | |
| 5,939,585 A | 8/1999 | Ditzel et al. | |
| 6,031,129 A | 2/2000 | Hinnenkamp et al. | |
| 6,130,355 A | 10/2000 | Jones | |
| 6,180,071 B1 | 1/2001 | Carey et al. | |
| 6,541,666 B2 | 4/2003 | Allan et al. | |
| 6,552,221 B1 | 4/2003 | Hallinan et al. | |
| 6,916,951 B2 | 7/2005 | Tustin et al. | |
| 7,053,241 B1 | 5/2006 | Torrence | |
| 7,115,774 B2 | 10/2006 | Magna et al. | |
| 7,208,605 B2 | 4/2007 | Davis, Jr. | |
| 7,253,304 B1 | 8/2007 | Tustin et al. | |
| 7,582,792 B2 | 9/2009 | Zoeller et al. | |
| 7,629,491 B2 | 12/2009 | Zoeller et al. | |
| 7,678,939 B2 | 3/2010 | Torrence | |
| 7,744,838 B2 | 6/2010 | Davis, Jr. | |
| 7,812,191 B2 | 10/2010 | Hallinan et al. | |
| 7,858,802 B2 | 12/2010 | Maase et al. | |
| 2003/0212295 A1 | 11/2003 | Charles et al. | |
| 2007/0293695 A1 | 12/2007 | Zoeller et al. | |

FOREIGN PATENT DOCUMENTS

| | | |
|---|---|---|
| EP | 0391680 A1 | 10/1990 |
| EP | 0506240 A2 | 9/1992 |
| EP | 1364936 A1 | 11/2003 |

* cited by examiner

*Primary Examiner* — Yevegeny Valenrod

(57) ABSTRACT

The disclosure relates to a process in which methanol is carbonylated in a reaction zone in the presence of a catalyst to obtain a reaction mixture (A) comprising acetic acid, hydrogen iodide, methyl iodide, water and the catalyst. At least a part of the reaction mixture (A) is withdrawn from the reaction zone. The withdrawn part of the reaction mixture (A) is introduced into a flash zone where it is brought into contact with an alkylimidazolium iodide to form a secondary mixture (B), and where the secondary mixture (B) is separated to obtain a vapor stream ($B_V$) which comprises the acetic acid, water and methyl iodide, and a liquid stream ($B_L$) which comprises the catalyst, the alkylimidazolium iodide and hydrogen iodide. The vapor stream ($B_V$) is processed to purify the acetic acid, and the liquid stream ($B_L$) is recycled to the reaction zone. The reaction mixture (A) is brought into contact with the alkylimidazolium iodide in the flash zone 1) by introducing to the flash zone separately from the withdrawn part of the reaction mixture (A) an extraneous alkylimidazolium iodide; or
2) by introducing to the flash zone separately from the withdrawn part of the reaction mixture (A) an alkylimidazole and forming the alkylimidazolium iodide in situ by reacting the alkylimidazole with the hydrogen iodide or the methyl iodide.

19 Claims, 5 Drawing Sheets

Figure 1:

$$CH_3OH + HI \rightleftharpoons CH_3I + H_2O \quad (A)$$

$$[Rh(CO)_2I_2]^- + CH_3I \longrightarrow [CH_3Rh(CO)_2I_3]^- \quad (B)$$

$$[CH_3Rh(CO)_2I_3]^- + CO \longrightarrow [CH_3C(O)Rh(CO)_2I_3]^- \quad (C)$$

$$[CH_3C(O)Rh(CO)_2I_3]^- \longrightarrow CH_3C(O)I + [Rh(CO)_2I_2]^- \quad (D)$$

$$CH_3C(O)I + H_2O \longrightarrow CH_3C(O)OH + HI \quad (E)$$

$$H_2O + CO \rightleftharpoons CO_2 + H_2 \quad (F)$$

$$CH_3C(O)OH + CH_3OH \longrightarrow CH_3C(O)OCH_3 \quad (G)$$

$$CH_3C(O)OCH_3 + HI \longrightarrow CH_3C(O)OH + CH_3I \quad (H)$$

PROCESS FOR THE PRODUCTION OF ACETIC ACID

FIELD OF THE INVENTION

The disclosure relates to the manufacture of acetic acid. More particularly, the disclosure relates to a process in which methanol is carbonylated in a reaction zone in the presence of a catalyst to obtain a reaction mixture (A) comprising acetic acid, hydrogen iodide, methyl iodide, water and the catalyst. At least a part of the reaction mixture (A) is withdrawn from the reaction zone. The withdrawn part of the reaction mixture (A) is introduced into a flash zone where it is brought into contact with an alkylimidazolium iodide to form a secondary mixture (B), and where the secondary mixture (B) is separated to obtain a vapor stream ($B_V$) which comprises the acetic acid, water and methyl iodide, and a liquid stream ($B_L$) which comprises the catalyst, the alkylimidazolium iodide and hydrogen iodide. The vapor stream ($B_V$) is processed to purify the acetic acid, and the liquid stream ($B_L$) is recycled to the reaction zone. The reaction mixture (A) is brought into contact with the alkylimidazolium iodide in the flash zone
1) by introducing to the flash zone separately from the withdrawn part of the reaction mixture (A) an extraneous alkylimidazolium iodide; or
2) by introducing to the flash zone separately from the withdrawn part of the reaction mixture (A) an alkylimidazole and forming the alkylimidazolium iodide in situ by reacting the alkylimidazole with the hydrogen iodide or the methyl iodide.

It has been found that the alkylimidazolium iodide interacts with hydrogen iodide and thus reduces the tendency of hydrogen iodide to become entrained in the vapor stream ($B_V$). Hydrogen iodide poses corrosion issues and is involved in the formation of long chain alkyl iodide by-products such as hexyl iodide which are hard to separate from acetic acid. The present process therefore alleviates corrosion problems as well as problems caused by the formation of undesired by-products. Additionally, the alkylimidazolium iodide has been found to reduce the volatilization of water thereby further facilitating the purification of acetic acid.

BACKGROUND OF THE INVENTION

The manufacture of acetic acid by carbonylating methanol in the presence of a catalyst is of major industrial importance as acetic acid is employed in a wide variety of applications. The reaction per se can be represented by:

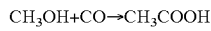
$$CH_3OH + CO \rightarrow CH_3COOH$$

However, the underlying chemistry is intricate and involves a multiplicity of interrelated reactions, by-products, and equilibria. To be practicable, a manufacturing process, therefore, has to balance those reactions, the associated by-products, and the purification of the product.

Prior to 1970, acetic acid was produced using a cobalt catalyst. A rhodium carbonyl iodide catalyst was developed in 1970 by Monsanto. The rhodium catalyst is considerably more active than the cobalt catalyst, which allows for lower reaction pressure and temperature. Most importantly, the rhodium catalyst exhibits high selectivity to acetic acid.

One of the problems associated with the original Monsanto process is that a large amount of water (about 14% by weight of the reaction mixture) is needed to produce hydrogen in the reactor via the water-gas shift reaction:

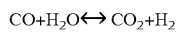
$$CO + H_2O \leftrightarrow CO_2 + H_2$$

Water and hydrogen react with precipitated Rh(III) and inactive $[Rh_4(CO)_2]$ and are necessary to regenerate the active Rh(I) catalyst. However, large amounts of water increase the formation of hydrogen iodide. Hydrogen iodide is a necessary intermediate in the reactions involved in the formation of acetic acid. However, increased amounts of hydrogen iodide are undesirable because it is highly corrosive and gives rise to engineering problems. Additionally, hydrogen iodide is involved in the formation of undesired by-products, in particular long-chain alkyl iodides such as hexyl iodide, which are hard to separate from the acetic acid product. Further, removing a large amount of water from the acetic acid product renders the process more costly.

In the late '70s Celanese modified the carbonylation process by introducing lithium iodide to the reaction mixture. Lithium iodide increases the catalyst stability by minimizing side reactions which produce inactive Rh(III) species. Consequently, the amount of water which is necessary to stabilize the catalyst can be reduced. Additionally, lithium iodide has been found to decrease the vaporization tendency of water. See, e.g., EP 506 240. The process, thus, has advantages with regard to the separation of water and acetic acid. However, the respective process modification does not alleviate the problems associated with hydrogen iodide.

In the early '90s, Millennium Petrochemicals developed a new rhodium carbonylation catalyst system that does not use a metal iodide as catalyst stabilizer. Instead, the catalyst system employs a pentavalent Group 15 oxide such as triphenylphosphine oxide as a catalyst stabilizer. The Millennium catalyst system not only reduces the amount of water needed for stabilizing the catalyst, but also increases the carbonylation rate and acetic acid yield. See, e.g., U.S. Pat. No. 5,817,869 and U.S. Pat. No. 6,031,129.

Further attempts to ensure stabilization of the catalyst while reducing the amount of water employed in the carbonylation of methanol involve the use of ionic liquids, i.e., phosphonium or ammonium salts, which are liquid under the conditions of the carbonylation reaction. The ionic liquids may serve as stabilizer, i.e., EP 391 680, U.S. Pat. No. 5,416,237, and U.S. Pat. No. 7,115,774, or as solvent, i.e., U.S. Pat. No. 6,916,951, U.S. Pat. No. 7,115,774.

In general, acetic acid is produced in a plant which can be conveniently divided into three functional areas, i.e., the reaction, the light ends recovery, and the purification. In general, the reaction area comprises a reactor or reaction zone and a flash tank or flash zone. The light ends recovery area comprises a light ends distillation column or fractioning zone and a phase separation vessel, e.g., a decanter. The light ends distillation column may also be part of the purification area, which in turn further comprises a drying column and optionally a heavy ends distillation column. A schematic illustration of an acetic acid plant is set forth in FIG. 1 of U.S. Pat. No. 6,552,221 which is herewith incorporated by reference.

In general, the flash tank or flash zone primarily serves to separate the catalyst and any catalyst stabilizer from the crude reaction mixture, whereas the light ends distillation column or fractioning zone serves to purify crude acetic acid which is obtained as a vapor stream in the flash zone, and to recover hydrogen iodide which otherwise may be lost from the process. Currently, hydrogen iodide is recovered primarily with the bottom stream formed in the fractioning zone which usually comprises acetic acid, water and hydrogen iodide. Hydrogen iodide forms a high boiling azeotrope in acetic acid solutions having greater than about 5 wt. % water. If the water concentration in the bottom stream falls below about 5 wt. %, azeotropic breakdown and hydrogen iodide volatilization occurs. Such volatilization leads to less hydrogen iodide in the bottom stream obtained in the fractioning zone and returned to the reaction zone, and thus, may adversely impact reactor iodide inventory. Also, volatilized hydrogen iodide becomes part of the aqueous acetic acid stream which is withdrawn from the fractioning zone for further purification. Process equipment generally used in the manufacture of acetic acid is substantially inert to the components. However, the equipment may be corroded or otherwise adversely affected when the amount of hydrogen iodide in the purification section reaches excessively high levels. Additionally, hydrogen iodide gives rise to the formation of long-chain alkyl iodide impurities such as, e.g., hexyl iodide, which are hard to remove and which complicate the purification of acetic acid. Thus, the presence of significant amounts of hydrogen iodide in the aqueous acetic acid which is recovered from the fractioning zone has consequences both in terms of corrosion of purification vessels and in terms of iodide and alkyl iodide contamination of the final acetic acid product.

It is desirable to reduce losses of hydrogen iodide from the reaction cycle, and to separate hydrogen iodide from the product stream as early as possible to prevent or at least significantly reduce the formation of alkyl iodide impurities. It is also desirable to alleviate corrosion problems caused by hydrogen iodide in the fractioning zone and downstream from the fractioning zone.

SUMMARY OF THE INVENTION

Accordingly, in a first aspect, the present disclosure provides a process for producing acetic acid which comprises:
(a) carbonylating methanol in the presence of a catalyst in a reaction zone to obtain a reaction zone to obtain a reaction mixture (A) comprising the acetic acid, hydrogen iodide, methyl iodide, water and the catalyst;
(b) withdrawing at least a part of the reaction mixture (A) from the reaction zone;
(c) introducing the withdrawn part of the reaction mixture (A) into a flash zone;
(d) contacting the withdrawn part of the reaction mixture (A) in the flash zone with an alkylimidazolium iodide to form a secondary mixture (B);
(e) separating the secondary mixture (B) in the flash zone to obtain a vapor stream ($B_V$) comprising acetic acid, water and methyl iodide, and a liquid stream ($B_L$) comprising the catalyst, the alkylimidazolium iodide and hydrogen iodide; and
(f) recycling the liquid stream ($B_L$) to the reaction zone;
wherein the reaction mixture (A) is brought into contact with the alkylimidazolium iodide in the flash zone
  1) by introducing to the flash zone separately from the withdrawn reaction mixture (A) an extraneous alkylimidazolium iodide; or
  2) by introducing to the flash zone separately from the withdrawn reaction mixture (A) an alkylimidazole and forming the alkylimidazolium iodide in situ by reacting the alkylimidazole with the hydrogen iodide and/or the methyl iodide.

In a second aspect, the present disclosure provides for a process in accordance with the foregoing aspect, wherein the withdrawn reaction mixture (A) is brought into contact with the alkylimidazolium iodide in the flash zone by introducing the extraneous alkylimidazolium iodide to the flash zone.

In a third aspect, the present disclosure provides for a process in accordance with either one of the foregoing aspects, wherein the extraneous alkylimidazolium iodide is a compound of formula (I)

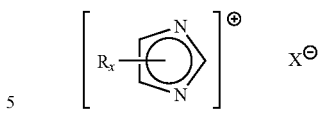

wherein x is 1, 2, 3 or 4, each R independently is $C_1$-$C_6$-alkyl, and $X^-$ is an iodine anion.

In a fourth aspect, the present disclosure provides for a process in accordance with either one of the foregoing aspects, wherein the extraneous alkylimidazolium iodide is a compound of formula (Ia)

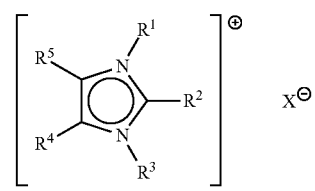

wherein
$R^1$ is hydrogen or $C_1$-$C_6$-alkyl;
$R^2$, $R^3$, $R^4$ and $R^5$, each independently, is hydrogen or $C_1$-$C_2$-alkyl; and
$X^-$ is an iodine anion;
and wherein at least one of $R^1$, $R^2$, $R^3$, $R^4$ and $R^5$ is different from hydrogen, and at least one of $R^1$, $R^2$, $R^3$, $R^4$ and $R^5$ denotes hydrogen.

In a fifth aspect, the present disclosure provides for a process in accordance with either one of the foregoing aspects, wherein the extraneous alkylimidazolium iodide is a hydrogen iodide or $C_1$-$C_6$-alkyl iodide salt of at least one alkylimidazole selected from the group consisting of 1-methylimidazole, 1-ethylimidazole, 1-propylimidazole, 1-isopropylimidazole, 1-(1-butyl)imidazole, 1-(2-butyl)imidazole, 1-isobutylimidazole, 1-tert-butylimidazole, 3-methylimidazole, 3-ethylimidazole, 4-methylimidazole, 4-ethylimidazole, 1,4-dimethylimidazole, 1,4-diethylimidazole, 1-ethyl-4-methylimidazole, 4-ethyl-1-methylimidazole, 2-methyl-1-propylimidazole, 4-methyl-1-propylimidazole, 5-methyl-1-propylimidazole, 2,4-dimethyl-1-propylimidazole, 2,5-dimethyl-1-propylimidazole, 1-isopropyl-2-methylimidazole, 1-isopropyl-4-methylimidazole, 1-isopropyl-5-methylimidazole, 2,4-dimethyl-1-isopropylimidazole, 2,5-dimethyl-1-isopropylimidazole, 1-(1-butyl)-2-methylimidazole, 1-(1-butyl)-4-methylimidazole, 1-(1-butyl)-5-methylimidazole, 1-(1-butyl)-2,4-dimethylimidazole, 1-(1-butyl)-2,5-dimethylimidazole, 1-(2-butyl)-2-methylimidazole, 1-(2-butyl)-4-methylimidazole, 1-(2-butyl)-5-methylimidazole, 1-(2-butyl)-2,4-dimethylimidazole, 1-(2-butyl)-2,5-dimethylimidazole, 1-isobutyl-2-methylimidazole, 1-isobutyl-4-methylimidazole, 1-isobutyl-5-methylimidazole, 1-isobutyl-2,4-dimethylimidazole, 1-isobutyl-2,5-dimethylimidazole, 1-tert-butyl-2-methylimidazole, 1-tert-butyl-4-methylimidazole, 1-tert-butyl-5-methylimidazole, 1-tert-butyl-2,4-dimethylimidazole, and 1-tert-butyl-2,5-dimethylimidazole.

In a sixth aspect, the present disclosure provides for a process in accordance with either one of the foregoing aspects, wherein the extraneous alkylimidazolium iodide is introduced to the flash zone separately and independently from any recycle stream which is recovered downstream of the flash zone.

In a seventh aspect, the present disclosure provides for a process in accordance with either one of the foregoing aspects, wherein the extraneous alkylimidazolium iodide is introduced to the flash zone by adding the extraneous alkylimidazolium iodide to a recycle stream recovered downstream of the flash zone and introducing the recycle stream comprising the added alkylimidazolium iodide to the flash zone.

In an eighth aspect, the present disclosure provides for a process in accordance with the first aspect, wherein the withdrawn reaction mixture (A) is brought into contact with the alkylimidazolium iodide in the flash zone by introducing the alkylimidazole to the flash zone and forming the alkylimidazolium iodide in situ.

In a ninth aspect, the present disclosure provides for a process in accordance with the first or eighth aspect, wherein the alkylimidazole is a compound of formula (II)

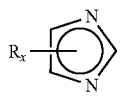

wherein x is 1, 2 or 3, and each R independently is $C_1$-$C_6$-alkyl.

In a tenth aspect, the present disclosure provides for a process in accordance with the first, eighth or ninth aspect, wherein the alkylimidazole is a compound of formula (IIa)

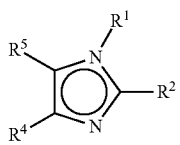

wherein
$R^1$ is hydrogen or $C_1$-$C_6$-alkyl;
$R^2$, $R^4$ and $R^5$, each independently, is hydrogen, or $C_1$-$C_2$-alkyl;
and wherein at least one of $R^1$, $R^2$, $R^4$ and $R^5$ is different from hydrogen, and at least one of $R^1$, $R^2$, $R^4$ and $R^5$ is hydrogen.

In an eleventh aspect, the present disclosure provides for a process in accordance with either one of the first, and eighth through tenth aspects, wherein the alkylimidazole is 1-methylimidazole, 1-ethylimidazole, 1-propylimidazole, 1-isopropylimidazole, 1-(1-butyl)imidazole, 1-(2-butyl)imidazole, 1-isobutylimidazole, 1-tert-butylimidazole, 3-methylimidazole, 3-ethylimidazole, 4-methylimidazole, 4-ethylimidazole, 1,4-dimethylimidazole, 1,4-diethylimidazole, 1-ethyl-4-methylimidazole, 4-ethyl-1-methylimidazole, 2-methyl-1-propylimidazole, 4-methyl-1-propylimidazole, 5-methyl-1-propylimidazole, 2,4-dimethyl-1-propylimidazole, 2,5-dimethyl-1-propylimidazole, 1-isopropyl-2-methylimidazole, 1-isopropyl-4-methylimidazole, 1-isopropyl-5-methylimidazole, 2,4-dimethyl-1-isopropylimidazole, 2,5-dimethyl-1-isopropylimidazole, 1-(1-butyl)-2-methylimidazole, 1-(1-butyl)-4-methylimidazole, 1-(1-butyl)-5-methylimidazole, 1-(1-butyl)-2,4-dimethylimidazole, 1-(1-butyl)-2,5-dimethylimidazole, 1-(2-butyl)-2-methylimidazole, 1-(2-butyl)-4-methylimidazole, 1-(2-butyl)-5-methylimidazole, 1-(2-butyl)-2,4-dimethylimidazole, 1-(2-butyl)-2,5-dimethylimidazole, 1-isobutyl-2-methylimidazole, 1-isobutyl-4-methylimidazole, 1-isobutyl-5-methylimidazole, 1-isobutyl-2,4-dimethylimidazole, 1-isobutyl-2,5-dimethylimidazole, 1-tert-butyl-2-methylimidazole, 1-tert-butyl-4-methylimidazole, 1-tert-butyl-5-methylimidazole, 1-tert-butyl-2,4-dimethylimidazole, and 1-tert-butyl-2,5-dimethylimidazole.

In a twelfth aspect, the present disclosure provides for a process in accordance with either one of the first, and eighth through eleventh aspects, wherein the alkylimidazole is introduced to the flash zone separately and independently from any recycle stream which is recovered downstream of the flash zone.

In a thirteenth aspect, the present disclosure provides for a process in accordance with either one of the first, and eighth through twelfth aspects, wherein the alkylimidazole is introduced to the flash zone by adding the alkylimidazole to a recycle stream recovered downstream of the flash zone and introducing the recycle stream comprising the added alkylimidazole or, where applicable, the corresponding alkylimidazolium iodide, to the flash zone.

In a fourteenth aspect, the present disclosure provides for a process in accordance with either one of the foregoing aspects, wherein the reaction mixture (A) does not comprise an alkylimidazolium iodide other than the alkylimidazolium iodide of the secondary mixture (B) which has been recycled to the reaction zone.

In a fifteenth aspect, the present disclosure provides for a process in accordance with either one of the foregoing aspects, wherein the catalyst is a rhodium catalyst.

In a sixteenth aspect, the present disclosure provides for a process in accordance with either one of the foregoing aspects, wherein the reaction mixture (A) comprises at least one catalyst stabilizer selected from the group consisting of phosphine oxides and iodides of a metal of Group 1 or 2 of the Periodic Table of the Elements.

In a seventeenth aspect, the present disclosure provides for a process in accordance with the sixteenth aspect, wherein the stabilizer is triphenylphosphine oxide and/or lithium iodide.

In an eighteenth aspect, the present disclosure provides for a process in accordance with either one of the foregoing aspects, wherein the reaction mixture (A) does not comprise a catalyst stabilizer selected from the group consisting of phosphine oxides and iodides of metals of Group 1 or 2 of the Periodic Table of the Elements.

In a nineteenth aspect, the present disclosure provides for a process in accordance with either one of the foregoing aspects, wherein the reaction mixture (A) comprises water in a concentration of from about 0.2% to about 10% by weight.

BRIEF DESCRIPTION OF THE DRAWINGS

FIG. 1 sets forth some of the interrelated reactions and equilibria believed to be involved in the carbonylation of methanol in the presence of a rhodium catalyst.

DETAILED DESCRIPTION OF THE INVENTION

Figure 2:
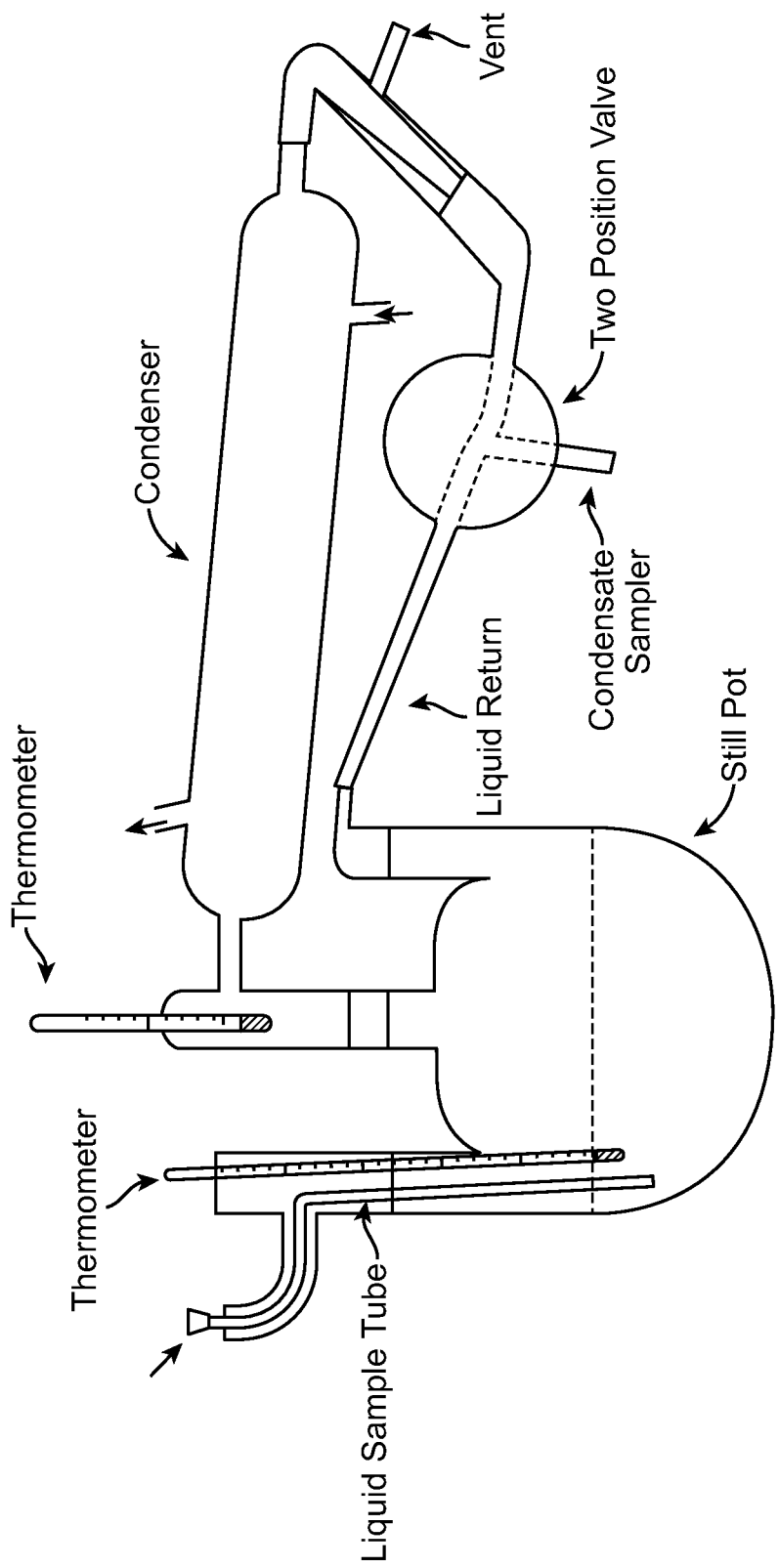
FIGS. 2 and 3 illustrate two recirculation apparatus for investigating the vapor liquid equilibrium (VLE).

A detailed description of embodiments of the present process follows. However, it is to be understood that the disclosed embodiments are merely exemplary of the process and that the process may be embodied in various and alternative forms of the disclosed embodiments. Therefore, specific procedural, structural and functional details which are addressed in the embodiments disclosed herein are not to be interpreted as limiting, but merely as a basis for the claims and as a representative basis for teaching one skilled in the art to variously employ the present process.

Unless specifically stated otherwise, all technical terms used herein have the meaning as commonly understood by those skilled in the art.

The designation of groups of the Periodic Table of the Elements as used herein is in accordance with the current IUPAC convention.

Moreover, unless specifically stated otherwise, the following expressions as used herein are understood to have the following meanings.

The expression "reaction zone" as used herein refers to at least one reactor or vessel in which methanol is carbonylated in the presence of a catalyst to form acetic acid at elevated pressure and temperature, i.e., the reactor(s) in the reaction area of an acetic acid producing plant.

The expression "flash zone" as used herein refers to at least one tank or vessel in which the reaction mixture obtained in the reaction zone is at least partially depressurized and/or cooled to form a vapor stream and a liquid stream, i.e., the flash tank(s) in the reaction area of an acetic acid producing plant.

The expression "fractioning zone" as used herein refers to at least one fractioning or distillation column, i.e., the light ends distillation column(s), in the light ends recovery area of an acetic acid producing plant.

The expression "liquid stream" as used herein refers to a product or composition which is in the liquid state under the conditions of the processing step in which the stream is formed.

Correspondingly, the expression "vapor stream" as used herein refers to a product or composition which is in the gaseous state under the conditions of the processing step in which the stream is formed.

The expression "recycle stream" as used herein refers to a product or composition which is recovered from a processing step downstream of the flash zone and which is recycled directly into the flash zone. The expression "recycle stream" herein excludes products and compositions which are recovered in a processing step downstream of the flash zone and which are recycled to a zone of the acetic acid production other than the flash zone, although such products and compositions may indirectly contribute to a recycle stream.

The expression "downstream of the flash zone" as used herein refers to all processing steps which are taken in the fractioning zone and in subsequent work-up or purification stages of the acetic acid production.

The expression "extraneous alkylimidazolium iodide" as used herein refers to an alkylimidazolium iodide which is newly introduced into the acetic acid production plant. In particular, the expression "extraneous alkylimidazolium iodide" herein excludes alkylimidazolium iodide which is used or generated in a zone or area of the acetic acid production other than the flash zone, and which is introduced to the flash zone by way of a recycle stream or by way of the reaction mixture (A). As such, the expression "extraneous alkylimidazolium iodide" as used herein also excludes alkylimidazolium iodide which has become part of the reaction mixture (A) due to recycling of the liquid stream ($B_L$).

The expression "alkylimidazole" as used herein refers to an imidazole in which at least one and at most three of the hydrogen atoms is or are replaced by an alkyl group. In this context, the expression "alkyl group" refers to straight chain or branched saturated hydrocarbon moieties, mono- or polycyclic saturated hydrocarbon moieties, as well as combinations thereof. Moreover, the reference to "alkylimidazole" in the singular is intended to include instances in which a combination of two or more alkylimidazoles is employed.

The expression "alkylimidazolium iodide" as used herein refers to an alkyl iodide or hydrogen iodide salt of an alkylimidazole as hereinabove specified. Moreover, unless specifically indicated otherwise, the expression "alkylimidazolium iodide" as used herein refers to the alkylimidazolium iodide which is brought into contact with the reaction mixture (A) in the flash zone to form the secondary mixture (B).

The expressions "OAc" or "AcO" are used herein as abbreviations for the acetate anion, i.e., $H_3CC(=O)O^-$.

The expression "acac" is used herein as an abbreviation for acetoacetate anion, i.e., $H_3CC(=O)CH_2C(=O)O^-$.

Unless specifically indicated otherwise, the expression "wt. %" as used herein refers to the percentage by weight of a particular component in the referenced composition.

With respect to all ranges disclosed herein, such ranges are intended to include any combination of the mentioned upper and lower limits even if the particular combination is not specifically listed.

All publications, patent applications, and patents mentioned herein are incorporated by reference in their entirety. In the event of conflict, the present specification, including definitions, is intended to control.

The process for producing acetic acid in accordance with the present invention involves (a) carbonylating methanol in the presence of a catalyst in a reaction zone to obtain a reaction zone to obtain a reaction mixture (A) comprising the acetic acid, hydrogen iodide, methyl iodide, water and the catalyst;

(b) withdrawing at least a part of the reaction mixture (A) from the reaction zone;

(c) introducing the withdrawn part of the reaction mixture (A) into a flash zone;

(d) contacting the withdrawn part of the reaction mixture (A) in the flash zone with an alkylimidazolium iodide to form a secondary mixture (B);

(e) separating the secondary mixture (B) in the flash zone to obtain a vapor stream ($B_V$) comprising acetic acid, water and methyl iodide, and a liquid stream ($B_L$) comprising the catalyst, the alkylimidazolium iodide and hydrogen iodide; and (f) recycling the liquid stream ($B_L$) to the reaction zone;

wherein the reaction mixture (A) is brought into contact with the alkylimidazolium iodide in the flash zone 1) by introducing to the flash zone separately from the withdrawn reaction mixture (A) an extraneous alkylimidazolium iodide; or 2) by introducing to the flash zone separately from the withdrawn reaction mixture (A) an alkylimidazole and forming the alkylimidazolium iodide in situ by reacting the alkylimidazole with the hydrogen iodide and/or the methyl iodide.

It has been found, surprisingly, that bringing the reaction mixture (A) into contact with an extraneous alkylimidazolium iodide or by forming the alkylimidazolium iodide in situ in the flash zone significantly reduces the amount of hydrogen iodide which becomes entrained in the vapor phase ($B_V$). As a consequence, the separation of hydrogen iodide in the fractioning zone is facilitated or becomes unnecessary. The alkylimidazolium iodide interacts with hydrogen iodide and, thus, reduces the tendency of hydrogen iodide to vaporize. The alkylimidazolium iodide itself is high boiling and therefore becomes part of the liquid stream ($B_L$) in the flash zone where it inhibits or at least significantly reduces the tendency of hydrogen iodide to vaporize. Additionally, when the alkylimidazolium iodide is formed in situ in the flash zone by bringing the reaction mixture (A) into contact with an alkylimidazole, the alkylimidazole acts as a scavenger of hydrogen iodide thereby further reducing the amount of hydrogen iodide which may become entrained in the vapor stream ($B_V$) and thus is carried forth into the fractioning zone. It has further been found, surprisingly, that the alkylimidazolium iodide does not significantly increase, and in some embodiments even reduces, the tendency of water to vaporize from the liquid stream ($B_L$). In some embodiments, the inhibiting effect of the alkylimidazolium iodide on the vaporization of hydrogen iodide is essentially similar to that of a pentavalent Group 15 oxide.

It has further been found that the alkylimidazolium iodide does not significantly increase, and in some embodiments even reduces, the tendency of water to vaporize from the bottom stream ($B_L$). In some embodiments, the inhibiting effect of the alkylimidazolium iodide on the vaporization of water is similar to that of lithium iodide.

The carbonylation reaction in accordance with the present disclosure is performed in the presence of a carbonylation catalyst and optionally a catalyst stabilizer. Suitable carbonylation catalysts include those known in the acetic acid industry. Examples of suitable carbonylation catalysts include rhodium catalysts and iridium catalysts.

Suitable rhodium catalysts are described, for example, in U.S. Pat. No. 5,817,869. Suitable rhodium catalysts include rhodium metal and rhodium compounds. Preferably, the rhodium compounds are selected from the group consisting of rhodium salts, rhodium oxides, rhodium acetates, organorhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, the like, and mixtures thereof. Most preferably, the rhodium compounds are selected from the group consisting of $[H]Rh(CO)_2I_2$, $Rh(CH_3CO_2)_2$, the like, and mixtures thereof.

Suitable iridium catalysts are described, for example, in U.S. Pat. No. 5,932,764. Suitable iridium catalysts include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3 \times 4H_2O$, $IrBr_3 \times 4H_2O$, $Ir_3(CO)_{12}$, $Ir_2O_3$, $IrO_2$, $Ir(acac)(CO)_2$, $Ir(acac)_3$, $Ir(OAc)_3$, $[Ir_3O(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates.

The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are acetates.

The reaction rate depends upon the concentration of the catalyst in the reaction mixture (A). The catalyst concentration normally is from about 1.0 mmol to about 100 mmol catalyst per liter (mmol/l) of (A). In some embodiments the catalyst concentration is at least 2.0 mmol/l, or at least 5.0 mmol/l, or at least 7.5 mmol/l. In some embodiments the catalyst concentration is at most 75 mmol/l, or at most 50 mmol/l, or at least 25 mmol/l. In particular embodiments, the catalyst concentration is from about 2.0 to about 75 mmol/l, or from about 5.0 to about 50 mmol/l, or from about 7.5 to about 25 mmol/l.

In some embodiments, the reaction is performed in the presence of a catalyst stabilizer. Suitable catalyst stabilizers include those known to the industry. In general, there are two types of catalyst stabilizers. The first type of catalyst stabilizer is a metal iodide salt, i.e., a iodide of a metal of Group 1 or 2 such as lithium iodide. The second type of catalyst stabilizer is a non-salt stabilizer. Preferred non-salt stabilizers are pentavalent Group 15 oxides. See U.S. Pat. No. 5,817,869. Phosphine oxides are more preferred. Triphenylphosphine oxides are most preferred.

The amount of metal iodide, when used, generally is such that a concentration of from about 1 to about 20 wt. % (about 0.1 to about 2.0 M) of the metal iodide is present in the reaction mixture. More preferably, this optional component is present in the reaction mixture in an amount of from about 5 to about 10 wt. % which corresponds to a molarity range of from about 0.5 to about 1.0 M.

The amount of pentavalent Group 15 oxide, when used, generally is such that its concentration to rhodium is greater than about 60:1. Preferably, the concentration of the pentavalent Group 15 oxide to rhodium is from about 60:1 to about 500:1. In some embodiments, from about 0.1 to about 3 M of the pentavalent Group 15 oxide is present in the reaction mixture. More preferably, from about 0.15 to about 1.5 M, or from 0.25 to 1.2 M, of the pentavalent Group 15 oxide is present in the reaction mixture.

In other embodiments, the reaction is performed in the absence of a stabilizer selected from the group of metal iodide salts and non-metal stabilizers such as pentavalent Group 15 oxides. In further embodiments, the catalyst stabilizer consists of the alkylimidazolium iodide which is brought into contact with the reaction mixture (A) in the flash zone.

The carbonylation reaction is preferably performed in the presence of water. Preferably, the concentration of water which is present in the reaction zone is from about 2 wt. % to about 14 wt. % based on the total weight of the reaction mixture (A). More preferably, the water concentration is from about 2 wt. % to about 10 wt. %. Most preferably, the water concentration is from about 3 wt. % to about 8 wt. %.

The reaction is preferably performed in the presence of methyl acetate. Methyl acetate can be formed in situ. Optionally, methyl acetate can be added as a starting material to the reaction mixture. Preferably, the concentration of methyl acetate is from about 2 wt. % to about 20 wt. % based on the total weight of the reaction mixture (A). More preferably, the concentration of methyl acetate is from about 2 wt. % to about 16 wt. %. Most preferably, the concentration of methyl acetate is from about 2 wt. % to about 8 wt. %. Alternatively, methyl acetate or a mixture of methyl acetate and methanol from by-product streams of the hydrolysis/methanolysis of polyvinyl acetate can be used for the carbonylation reaction.

The reaction is performed in the presence of methyl iodide. Methyl iodide acts as a catalyst promoter. Preferably, the concentration of methyl iodide is from about 0.6 wt. % to about 36 wt. % based on the total weight of the reaction mixture (A). More preferably, the concentration of methyl iodide is from about 4 wt. % to about 24 wt. %. Most preferably, the concentration of methyl iodide is from about 6 wt. % to about 20 wt. %. Alternatively, methyl iodide can be generated in the carbonylation reactor or reaction zone by adding hydrogen iodide.

Hydrogen may also be fed into the reaction zone. Addition of hydrogen can enhance the carbonylation efficiency. Preferably, the concentration of hydrogen is from about 0.1 mol % to about 5 mol % of carbon monoxide in the reaction zone. More preferably, the concentration of hydrogen is from about 0.3 mol % to about 3 mol % of carbon monoxide in the reaction zone.

Methanol and carbon monoxide are fed to the carbonylation reactor or reaction zone. The methanol feed to the carbonylation reaction can come from a syngas-methanol facility or any other source. Methanol does not react directly with carbon monoxide to form acetic acid. It is converted to methyl iodide by the hydrogen iodide present in the reaction zone and then reacts with carbon monoxide and water to give acetic acid and regenerate hydrogen iodide. Carbon monoxide not only becomes part of the acetic acid molecule, but it also plays an important role in the formation and stability of the active catalyst.

The carbonylation reaction is preferably performed at a temperature of about 120° C. to about 250° C. More preferably, the reaction is performed at a temperature of about 150° C. to about 200° C.

The carbonylation reaction is preferably performed under a pressure of about 200 psig to about 2,000 psig. More preferably, the reaction is performed under a pressure of about 300 psig to about 500 psig.

While the process may be performed batch-wise, it is preferable to operate the process continuously. Thus, at least a part of the reaction mixture (A) which is obtained in the carbonylation reaction is withdrawn from the reaction zone and is contacted in the flash zone with the alkylimidazolium iodide to form the secondary mixture (B), which secondary mixture (B) is separated, by flash separation in the flash zone, to obtain the liquid stream ($B_L$). The liquid stream ($B_L$) comprises the catalyst and the alkylimidazolium iodide as well as hydrogen iodide associated therewith and water, and is preferably returned to the reaction zone. The vapor stream ($B_V$) which is formed in the flash zone and which comprises acetic acid, water and methyl iodide is conveyed to the fractioning zone for further purification.

The flash zone is preferably maintained at a pressure below that of the reaction zone, typically at a pressure of from about 10 to 100 psig. The flash zone is preferably maintained at a temperature of from about 100 to 160° C. The flash zone optionally comprises, in addition to the at least one tank or vessel, a distillation column having at least 2 trays, and preferably 2 to 5 trays.

In one embodiment of the present process, the withdrawn reaction mixture (A) is brought into contact with the alkylimidazolium iodide in the flash zone, and the secondary mixture (B) is formed, by introducing an extraneous alkylimidazolium iodide to the flash zone.

In accordance with some embodiments, the extraneous alkylimidazolium iodide is a compound of formula (I)

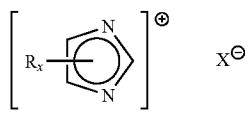

wherein $X^-$ is an iodine anion [$I^-$], x is 1, 2, 3 or 4, each R independently is $C_1$-$C_6$-alkyl, i.e., methyl, ethyl, propyl, 1-methylethyl, 1-butyl, 2-butyl, 1-(2-methyl)propyl, 2-(2-methyl)propyl, 1-pentyl, 2-pentyl, 3-pentyl, 1-(2-methyl)butyl, 1-(3-methyl)butyl, 2-(2-methyl)butyl, 2-(3-methyl)butyl, 1-(2,2-dimethyl)propyl, 1-hexyl, 2-hexyl, 3-hexyl, 1-(2-methyl)pentyl, 1-(3-methyl)pentyl, 1-(4-methyl)pentyl, 2-(2-methyl)pentyl, 2-(3-methyl)pentyl, 2-(4-methyl)pentyl, 3-(2-methyl)pentyl, 1-(2,2-dimethyl)butyl, 1-(2,3-dimethyl)butyl, 1-(3,3-dimethyl)butyl, 2-(2,3-dimethyl)butyl, 1-(2-ethyl)butyl, and 2-(2-ethyl)butyl.

In further embodiments; the extraneous alkylimidazolium iodide is a compound of formula (Ia)

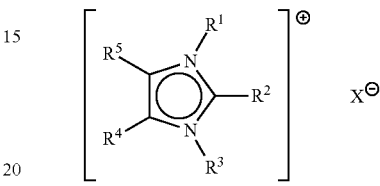

wherein
$X^-$ is an iodine anion [$I^-$];
$R^1$ is hydrogen or $C_1$-$C_6$-alkyl, in particular hydrogen or $C_1$-$C_4$-alkyl, i.e., hydrogen, methyl, ethyl, propyl, 1-methylethyl, 1-butyl, 2-butyl, 1-(2-methyl)propyl, and 2-(2-methyl)propyl; and
$R^2$, $R^3$, $R^4$ and $R^5$, each independently, is hydrogen or $C_1$-$C_2$-alkyl, i.e., hydrogen, methyl or ethyl;
wherein at least one of $R^1$, $R^2$, $R^3$, $R^4$ and $R^5$ is different from hydrogen, and at least one of $R^1$, $R^2$, $R^3$, $R^4$ and $R^5$ denotes hydrogen.

In yet further embodiments, the extraneous alkylimidazolium iodide (I) or (Ia) is a hydrogen iodide or $C_1$-$C_6$-alkyl iodide salt of at least one alkylimidazole selected from the group consisting of 1-methylimidazole, 1-ethylimidazole, 1-propylimidazole, 1-isopropylimidazole, 1-(1-butyl)imidazole, 1-(2-butyl)imidazole, 1-isobutylimidazole, 1-tert-butylimidazole, 3-methylimidazole, 3-ethylimidazole, 4-methylimidazole, 4-ethylimidazole, 1,4-dimethylimidazole, 1,4-diethylimidazole, 1-ethyl-4-methylimidazole, 4-ethyl-1-methylimidazole, 2-methyl-1-propylimidazole, 4-methyl-1-propylimidazole, 5-methyl-1-propylimidazole, 2,4-dimethyl-1-propylimidazole, 2,5-dimethyl-1-propylimidazole, 1-isopropyl-2-methylimidazole, 1-isopropyl-4-methylimidazole, 1-isopropyl-5-methylimidazole, 2,4-dimethyl-1-isopropylimidazole, 2,5-dimethyl-1-isopropylimidazole, 1-(1-butyl)-2-methylimidazole, 1-(1-butyl)-4-methylimidazole, 1-(1-butyl)-5-methylimidazole, 1-(1-butyl)-2,4-dimethylimidazole, 1-(1-butyl)-2,5-dimethylimidazole, 1-(2-butyl)-2-methylimidazole, 1-(2-butyl)-4-methylimidazole, 1-(2-butyl)-5-methylimidazole, 1-(2-butyl)-2,4-dimethylimidazole, 1-(2-butyl)-2,5-dimethylimidazole, 1-isobutyl-2-methylimidazole, 1-isobutyl-4-methylimidazole, 1-isobutyl-5-methylimidazole, 1-isobutyl-2,4-dimethylimidazole, 1-isobutyl-2,5-dimethylimidazole, 1-tert-butyl-2-methylimidazole, 1-tert-butyl-4-methylimidazole, 1-tert-butyl-5-methylimidazole, 1-tert-butyl-2,4-dimethylimidazole, and 1-tert-butyl-2,5-dimethylimidazole.

In some embodiments, the extraneous alkylimidazolium iodide is introduced to the flash zone separately and independently from any recycle stream which is recovered downstream of the flash zone.

In other embodiments, the extraneous alkylimidazolium iodide is introduced to the flash zone by adding the extraneous alkylimidazolium iodide to a recycle stream recovered downstream of the flash zone, and subsequently introducing the recycle stream comprising the added alkylimidazolium iodide to the flash zone.

In an alternative embodiment, the withdrawn reaction mixture (A) is brought into contact with the alkylimidazolium iodide, and the secondary mixture (B) is formed, in the flash zone by introducing an alkylimidazole to the flash zone and forming the alkylimidazolium iodide in situ.

In accordance with some embodiments, the alkylimidazole is a compound of formula (II)

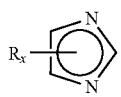

wherein x is 1, 2 or 3, and each R independently is $C_1$-$C_6$-alkyl, i.e., methyl, ethyl, propyl, 1-methylethyl, 1-butyl, 2-butyl, 1-(2-methyl)propyl, 2-(2-methyl)propyl, 1-pentyl, 2-pentyl, 3-pentyl, 1-(2-methyl)butyl, 1-(3-methyl)butyl, 2-(2-methyl)butyl, 2-(3-methyl)butyl, 1-(2,2-dimethyl)propyl, 1-hexyl, 2-hexyl, 3-hexyl, 1-(2-methyl)pentyl, 1-(3-methyl)pentyl, 1-(4-methyl)pentyl, 2-(2-methyl)pentyl, 2-(3-methyl)pentyl, 2-(4-methyl)pentyl, 3-(2-methyl)pentyl, 1-(2,2-dimethyl)butyl, 1-(2,3-dimethyl)butyl, 1-(3,3-dimethyl)butyl, 2-(2,3-dimethyl)butyl, 1-(2-ethyl)butyl, and 2-(2-ethyl)butyl.

In further embodiments, the alkylimidazole is a compound of formula (IIa)

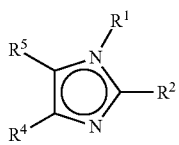

wherein
$R^1$ is hydrogen or $C_1$-$C_6$-alkyl, in particular hydrogen or $C_1$-$C_4$-alkyl, i.e., hydrogen, methyl, ethyl, propyl, 1-methylethyl, 1-butyl, 2-butyl, 1-(2-methyl)propyl, and 2-(2-methyl)propyl; and
$R^2$, $R^4$ and $R^5$, each independently, is hydrogen, or $C_1$-$C_2$-alkyl, i.e., hydrogen, methyl or ethyl;
wherein at least one of $R^1$, $R^2$, $R^4$ and $R^5$ is different from hydrogen, and at least one of $R^1$, $R^2$, $R^4$ and $R^5$ is hydrogen.

In yet further embodiments, the alkylimidazole (II) or (IIa) is 1-methylimidazole, 1-ethylimidazole, 1-propylimidazole, 1-isopropylimidazole, 1-(1-butyl)imidazole, 1-(2-butyl)imidazole, 1-isobutylimidazole, 1-tert-butylimidazole, 3-methylimidazole, 3-ethylimidazole, 4-methylimidazole, 4-ethylimidazole, 1,4-dimethylimidazole, 1,4-diethylimidazole, 1-ethyl-4-methylimidazole, 4-ethyl-1-methylimidazole, 2-methyl-1-propylimidazole, 4-methyl-1-propylimidazole, 5-methyl-1-propylimidazole, 2,4-dimethyl-1-propylimidazole, 2,5-dimethyl-1-propylimidazole, 1-isopropyl-2-methylimidazole, 1-isopropyl-4-methylimidazole, 1-isopropyl-5-methylimidazole, 2,4-dimethyl-1-isopropylimidazole, 2,5-dimethyl-1-isopropylimidazole, 1-(1-butyl)-2-methylimidazole, 1-(1-butyl)-4-methylimidazole, 1-(1-butyl)-5-methylimidazole, 1-(1-butyl)-2,4-dimethylimidazole, 1-(1-butyl)-2,5-dimethylimidazole, 1-(2-butyl)-2-methylimidazole, 1-(2-butyl)-4-methylimidazole, 1-(2-butyl)-5-methylimidazole, 1-(2-butyl)-2,4-dimethylimidazole, 1-(2-butyl)-2,5-dimethylimidazole, 1-isobutyl-2-methylimidazole, 1-isobutyl-4-methylimidazole, 1-isobutyl-5-methylimidazole, 2,4-dimethyl-1-isobutylimidazole, 2,5-dimethyl-1-isobutylimidazole, 1-tert-butyl-2-methylimidazole, 1-tert-butyl-4-methylimidazole, 1-tert-butyl-5-methylimidazole, 1-tert-butyl-2,4-dimethylimidazole, or 1-tert-butyl-2,5-dimethylimidazole.

In some embodiments, the alkylimidazole is introduced to the flash zone separately and independently from any recycle stream which is recovered downstream of the flash zone.

In other embodiments, the alkylimidazole is introduced to the flash zone by adding the alkylimidazole to a recycle stream recovered downstream of the flash zone and introducing the recycle stream comprising the added alkylimidazole or, where applicable, the corresponding alkylimidazolium iodide, to the flash zone.

Typically, the alkylimidazolium iodide forms when the alkylimidazole is brought into contact with hydrogen iodide and/or methyl iodide contained in the reaction mixture (A) or contained in a recycle stream. The reaction of the alkylimidazole with hydrogen iodide or methyl iodide is rapid and is generally quantitative at a temperature of about 20° C. Normally, the reaction takes place when the alkylimidazole is brought into contact with the reaction mixture (A) and, thus, is brought into contact with hydrogen iodide and methyl iodide.

In some embodiments, the reaction mixture (A) does not comprise an alkylimidazolium iodide other than the alkylimidazolium iodide of the liquid stream ($B_L$) which has been recycled to the reaction zone.

The extraneous alkylimidazolium iodide and the alkylimidazole can be employed in substance or in diluted form in combination of a solvent or diluent. The nature of the solvent or diluent generally is not critical so long as the solvent or diluent does not interfere with the carbonylation reaction or the purification of the acetic acid. Preferably, no solvent or diluent is used, or the solvent or diluent is one or more of the liquid constituents of the reaction mixture (A), e.g., acetic acid, methanol, methyl iodide and water, preferably acetic acid and/or methanol. Similarly, the amount of solvent or diluents used in this context is not critical and may be adjusted broadly depending on process economy. The use of a solvent or diluent may be advantageous to ensure fast and even distribution and contact of the extraneous alkylimidazolium iodide or the alkylimidazole with the withdrawn reaction mixture (A) in the flash zone. Thus, when the extraneous alkylimidazolium iodide or the alkylimidazole is introduced to the flash zone separately and independently from the reaction mixture (A) and from any recycle stream it may be advantageous to employ a solvent or diluent. On the other hand, when the extraneous alkylimidazolium iodide or the alkylimidazole is brought into contact with the reaction mixture (A) in the flash zone by adding it to a recycle stream prior to introducing the modified recycle stream to the flash zone, it may be advantageous to employ the extraneous alkylimidazolium iodide or the alkylimidazole in substance, i.e., in undiluted form, as the liquid constituents of the recycle stream act as solvents or diluents.

The amount of alkylimidazolium iodide which is brought into contact with the reaction mixture (A) in the flash zone is generally not critical so long as the alkylimidazolium iodide is provided in an effective amount. An effective amount in this context is the amount of alkylimidazolium iodide which is capable of scavenging at least a part of the hydrogen iodide which is present in the reaction mixture (A) by way of an interaction of the extraneous alkylimidazolium iodide and the hydrogen iodide. Where the alkylimidazolium iodide is generated in situ, an effective amount is the amount of alkylimidazole which is capable of scavenging at least a part of the hydrogen iodide which is present in the reaction mixture (A), by way of generating the alkylimidazolium iodide in situ and/or by way of an interaction of the extraneous alkylimidazolium iodide and the hydrogen iodide.

In some embodiments, the amount of alkylimidazolium iodide which is brought into contact with the reaction mixture (A) in the flash zone is adjusted depending on the hydrogen iodide content of the reaction mixture (A). In some embodiments, the alkylimidazolium iodide is employed in an amount of at least about 0.1 mol per mol hydrogen iodide. In alternative embodiments, at least about 0.5 mol alkylimidazolium iodide, or at least about 1 mol alkylimidazolium iodide, per mol hydrogen iodide is employed. Generally, it is not detrimental to the subsequent separation and purification of the acetic acid product if the molar amount of alkylimidazole exceeds the molar amount in which hydrogen iodide is present, even if the excess in which the alkylimidazole is added is significant so long as the boiling point of the alkylimidazolium iodide is sufficiently higher than the boiling point of the crude acetic acid which is withdrawn from the flash zone. Normally, the boiling point of the alkylimidazolium iodide in degree Celsius is sufficiently higher when the boiling point is at least 15°, or at least 30°, or at least 50°, above the boiling point of the crude acetic acid in degree Celsius. In particular variants of these embodiments, the alkylimidazolium iodide is employed in an amount of from about 0.1 to about 10 mol per mol hydrogen iodide. In alternative variants, the amount of alkylimidazolium iodide is from about 0.25 to about 7.5 mol, or from about 0.5 to about 5 mol, or from about 0.75 to about 2.5 mol, per mol hydrogen iodide. In further alternative embodiments, the amount of alkylimidazolium iodide is from about 1 to about 10 mol, or from about 1 to about 7.5 mol, or from about 1 to about 5 mol, per mol hydrogen iodide.

In other embodiments, the alkylimidazolium iodide is brought into contact with the reaction mixture (A) in an amount of at least about 0.1 mol per mol hydrogen iodide. In alternative embodiments, at least about 0.5 mol alkylimidazolium iodide, or at least about 1 mol alkylimidazolium iodide, or at least about 1.5 mol alkylimidazole, per mol hydrogen iodide is employed. In particular variants of these embodiments, the alkylimidazolium iodide is employed in an amount from about 0.1 to about 1.5 mol per mol hydrogen iodide. In alternative variants, the amount of alkylimidazolium iodide is from about 0.1 to about 1.3 mol, or from about 0.1 to about 1.1 mol, per mol hydrogen iodide. In further alternative embodiments, the amount of alkylimidazolium iodide is from about 0.5 to about 3 mol, or from about 0.5 to about 2 mol, or from about 0.5 to about 1.5 mol, per mol hydrogen iodide.

In yet further embodiments, the alkylimidazole is brought into contact with the reaction mixture (A) in the flash zone in an amount of at least about 0.1 mol per mol hydrogen iodide. In alternative embodiments, at least about 0.5 mol alkylimidazole, or at least about 1 mol alkylimidazole, or at least about 1.5 mol alkylimidazole, per mol hydrogen iodide is employed. Generally, it is not detrimental to the subsequent separation and purification of the acetic acid product if the molar amount of alkylimidazole exceeds the molar amount in which hydrogen iodide is present, even if the excess in which the alkylimidazole is added is significant so long as the boiling point of the alkylimidazole is sufficiently higher than the boiling point of the crude acetic acid which is withdrawn from the fractioning zone. In particular variants of these embodiments, the alkylimidazole is brought into contact with the reaction mixture (A) in the flash zone in an amount from about 0.1 to about 1.5 mol per mol hydrogen iodide. In alternative variants, the amount of alkylimidazole is from about 0.1 to about 1.3 mol, or from about 0.1 to about 1.1 mol, per mol hydrogen iodide. In further alternative embodiments, the amount of alkylimidazole is from about 0.5 to about 3 mol, or from about 0.5 to about 2 mol, or from about 0.5 to about 1.5 mol, per mol hydrogen iodide.

In further embodiments, the alkylimidazolium iodide is brought into contact with the reaction mixture (A) in the flash zone in an amount sufficient to establish a concentration of no more than about 20 wt. % of the alkylimidazolium iodide in the liquid stream ($B_L$). In alternative embodiments, the alkylimidazolium iodide is contacted with (A) in an amount sufficient to establish a concentration of no more than about 15 wt. %, or no more than about 12 wt. %, or no more than about 10 wt. %, of the alkylimidazolium iodide in the liquid stream ($B_L$). In other embodiments, the alkylimidazolium iodide is brought into contact with the reaction mixture (A) in an amount sufficient to establish a concentration of at least about 0.5 wt. % of the alkylimidazolium iodide in the reaction liquid stream ($B_L$). In alternative embodiments, the alkylimidazolium iodide is contacted with (A) in an amount sufficient to establish a concentration of at least about 1 wt. %, or at least about 2.5 wt. %, or at least about 4 wt. %, of the alkylimidazolium iodide in the liquid stream ($B_L$). In particular embodiments, the alkylimidazolium iodide is brought into contact with the reaction mixture (A) in an amount sufficient to establish a concentration of from about 0.5 wt. % to about 20 wt. % of the alkylimidazolium iodide in the liquid stream ($B_L$).

In alternative embodiments, the alkylimidazolium iodide is contacted with (A) in an amount sufficient to establish a concentration of from about 1 wt. % to about 20 wt. %, or from about 2.5 wt. % to about 20 wt. %, or from about 4 wt. % to about 20 wt. %, of the alkylimidazolium iodide in the liquid stream ($B_L$). In alternative embodiments, the alkylimidazolium iodide is contacted with (A) in an amount sufficient to establish a concentration of from about 0.5 wt. % to about 15 wt. %, or from about 1 wt. % to about 15 wt. %, or from about 2.5 wt. % to about 15 wt. %, or from about 4 wt. % to about 15 wt. %, of the alkylimidazolium iodide in the liquid stream ($B_L$). In alternative embodiments, the alkylimidazolium iodide is contacted with (A) in an amount sufficient to establish a concentration of from about 0.5 wt. % to about 12 wt. %, or from about 1 wt. % to about 12 wt. %, or from about 2.5 wt. % to about 12 wt. %, or from about 4 wt. % to about 12 wt. %, of the alkylimidazolium iodide in the liquid stream ($B_L$).

The liquid stream ($B_L$) can be recycled to the reaction zone. The recycled liquid stream ($B_L$) introduces the alkylimidazolium iodide into the reaction zone, and consequently into the reaction mixture (A).

In certain embodiments, the amount of the alkylimidazolium iodide which is brought into contact with the reaction mixture (A) in the flash zone is adjusted to establish a steady state concentration of no more than about 20 wt. % of the alkylimidazolium iodide in the reaction mixture (A). In alternative embodiments, the alkylimidazolium iodide is brought into contact with the reaction mixture (A) in the flash zone in an amount sufficient to establish a steady state concentration of no more than about 17 wt. %, or no more than about 15 wt. %, or no more than about 12 wt. %, of the alkylimidazolium iodide in the reaction mixture (A). In other embodiments, the alkylimidazolium iodide is brought into contact with the reaction mixture (A) in the flash zone in an amount sufficient to establish a steady state concentration of at least about 2 wt. % of the alkylimidazolium iodide in the reaction mixture (A). In alternative embodiments, the alkylimidazolium iodide is brought into contact with the reaction mixture (A) in the flash zone in an amount sufficient to establish a steady state concentration of at least about 5 wt. %, or at least about 7 wt. %, of the alkylimidazolium iodide in the reaction mixture (A).

In particular embodiments, the alkylimidazolium iodide is brought into contact with the reaction mixture (A) in the flash zone in an amount sufficient to establish a steady state concentration from about 2 wt. % to about 20 wt. % of the alkylimidazolium iodide in the reaction mixture (A). In alternative embodiments, the alkylimidazolium iodide is brought into contact with the reaction mixture (A) in the flash zone in an amount sufficient to establish a steady state concentration of from about 5 wt. % to about 20 wt. %, or from about 7 wt. % to about 20 wt. %, of the alkylimidazolium iodide in the reaction mixture (A). In alternative embodiments, the alkylimidazolium iodide is brought into contact with the reaction mixture (A) in the flash zone in an amount sufficient to establish a steady state concentration of from about 2 wt. % to about 17 wt. %, or from about 5 wt. % to about 17 wt. %, or from about 7 wt. % to about 17 wt. %, of the alkylimidazolium iodide in the reaction mixture (A). In alternative embodiments, the alkylimidazolium iodide is brought into contact with the reaction mixture (A) in the flash zone in an amount sufficient to establish a steady state concentration of from about 2 wt. % to about 15 wt. %, or from about 5 wt. % to about 15 wt. %, or from about 7 wt. % to about 15 wt. %, of the alkylimidazolium iodide in the reaction mixture (A). In alternative embodiments, the alkylimidazolium iodide is brought into contact with the reaction mixture (A) in the flash zone in an amount sufficient to establish a steady state concentration of from about 2 wt. % to about 12 wt. %, or from about 5 wt. % to about 12 wt. %, or from about 7 wt. % to about 12 wt. %, of the alkylimidazolium iodide in the reaction mixture (A).

In general, the alkylimidazolium iodide can be brought into contact with the reaction mixture (A) in the flash zone either batch-wise or continuously. In some embodiments, the alkylimidazolium iodide is contacted with the reaction mixture (A) in the flash zone batch-wise throughout the process. In other embodiments, the alkylimidazolium iodide is brought into contact with the reaction mixture (A) in the flash zone continuously until the desired steady state concentration of the alkylimidazolium iodide in the reaction mixture (A) in the reaction zone is established, and will be contacted continuously or batch wise thereafter.

While it was known in the art that certain salts of alkylimidazoles can be employed as catalyst stabilizer, the process in accordance with the present disclosure differs from the prior art procedures at least in that extraneous alkylimidazolium iodide or alkylimidazole is brought into contact with the reaction mixture (A) in the flash zone. Moreover, the process in accordance with the present disclosure yields advantages which could not have been foreseen. The alkylimidazolium iodide which is brought into contact with the reaction mixture (A) in the flash zone acts as scavenger for hydrogen iodide, thus reducing the amount of hydrogen iodide which becomes entrained in the vapor stream ($B_V$). Thereby, considerably less hydrogen iodide, if any, is carried forth into the fractioning zone. Residual hydrogen iodide which may reach the fractioning zone is more easily separated from the product stream as a bottom product of the fractioning zone. Also, due to the removal of hydrogen iodide from the product stream in the earliest stage of the acetic acid work-up, side reactions which are caused by hydrogen iodide, i.e., the formation of undesirable long chain alkyl iodide contaminants in the product stream downstream from the flash zone, are significantly reduced. Additionally, the reduced amounts of hydrogen iodide in the product streams downstream from the flash zone alleviate corrosion and engineering problems. Also, the alkylimidazolium iodide acts as a catalyst stabilizer. Therefore, problems caused by losses of catalyst due to deactivation or deposition are reduced or may even be avoided.

The beneficial effect of the alkylimidazolium iodide on the vaporization of hydrogen iodide is not restricted to the flash zone. Rather, as the alkylimidazolium iodide becomes part of the reaction mixture (A) by recycling the liquid stream ($B_L$) from the flash zone to the reaction zone, its presence in the reaction mixture aids in reducing the tendency of hydrogen iodide to vaporize in the flash zone, thus aiding in reducing the amount of hydrogen iodide which may become entrained in the vapor stream ($B_V$). Therefore, upon continuous operation of the process, the amount of alkylimidazolium iodide which is brought into contact with the reaction mixture (A) in the flash zone normally may be decreased as steady state conditions are achieved. Under steady state conditions, the amount of alkylimidazolium iodide which is brought into contact with the reaction mixture (A) in the flash zone normally can be reduced to amounts necessary to maintain the desired steady state concentration of the alkylimidazolium iodide.

DETAILED DESCRIPTION OF THE DRAWINGS

FIG. 1 sets forth some of the interrelated reactions and equilibria believed to be involved in the carbonylation of methanol in the presence of a rhodium catalyst. Those having ordinary skill in the particular art will appreciate that further reactions and equilibria are involved and that the reproduced reactions are merely an illustration of the complexity of the multiplicity of interrelated reactions, by-products and equilibria.

FIG. 2 illustrates a diagrammatic first recirculation apparatus (Apparatus 1) for investigating the vapor liquid equilibrium (VLE). The apparatus comprises a 3-neck round-bottomed flask (Still Pot). The first neck is equipped with a tube (Liquid Sample Tube) for adding components to the liquid, or withdrawing samples from the liquid contained in the flask, and a thermometer measuring the temperature of the liquid contained in the flask. The second neck is equipped with a reflux/distillation head, and with a thermometer measuring the temperature of the vapor phase. The vapor is condensed in a condenser, and the condensate is conveyed back to the flask via a liquid return (Liquid Return) to the third neck of the flask. The liquid return is equipped with a vent (Vent) and a two position valve (Two Position Valve) for withdrawing samples of the condensate.

Figure 3:
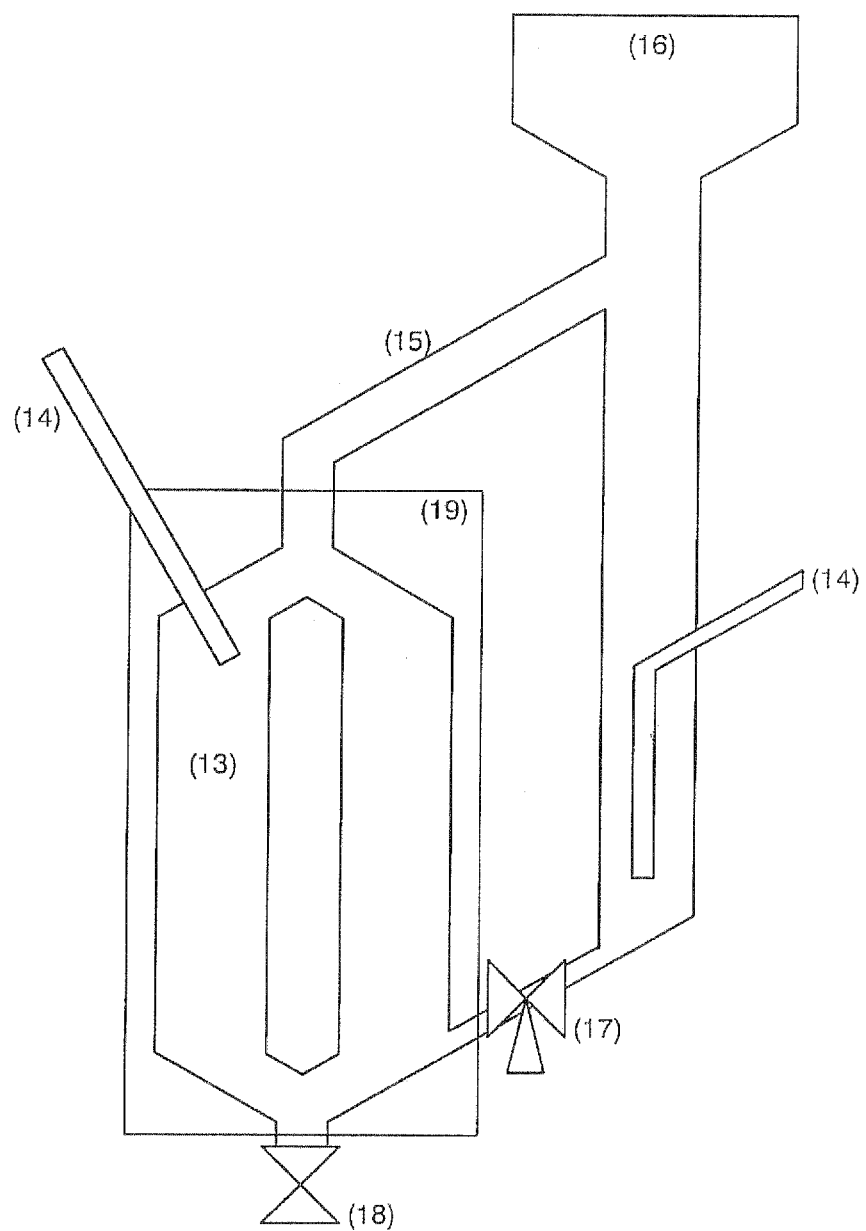

FIG. 3 illustrates a diagrammatic second recirculation apparatus (Apparatus 2) for investigating the vapor liquid equilibrium (VLE). The apparatus comprises a dual chambered circulation volume (13) as the still. The still is equipped with a recirculation line (15) which, in turn, connects to a condenser (16) and comprises a two position valve (17) for sampling the condensate. Additionally, the still is equipped with a bottom tap (18) for sampling the liquid. The still is enclosed by heating and insulating means (19). Both, the still (13) and the recirculation line (15) are provided with thermowells with thermocouples (14) connected to a temperature control unit (not shown).

Figure 4:
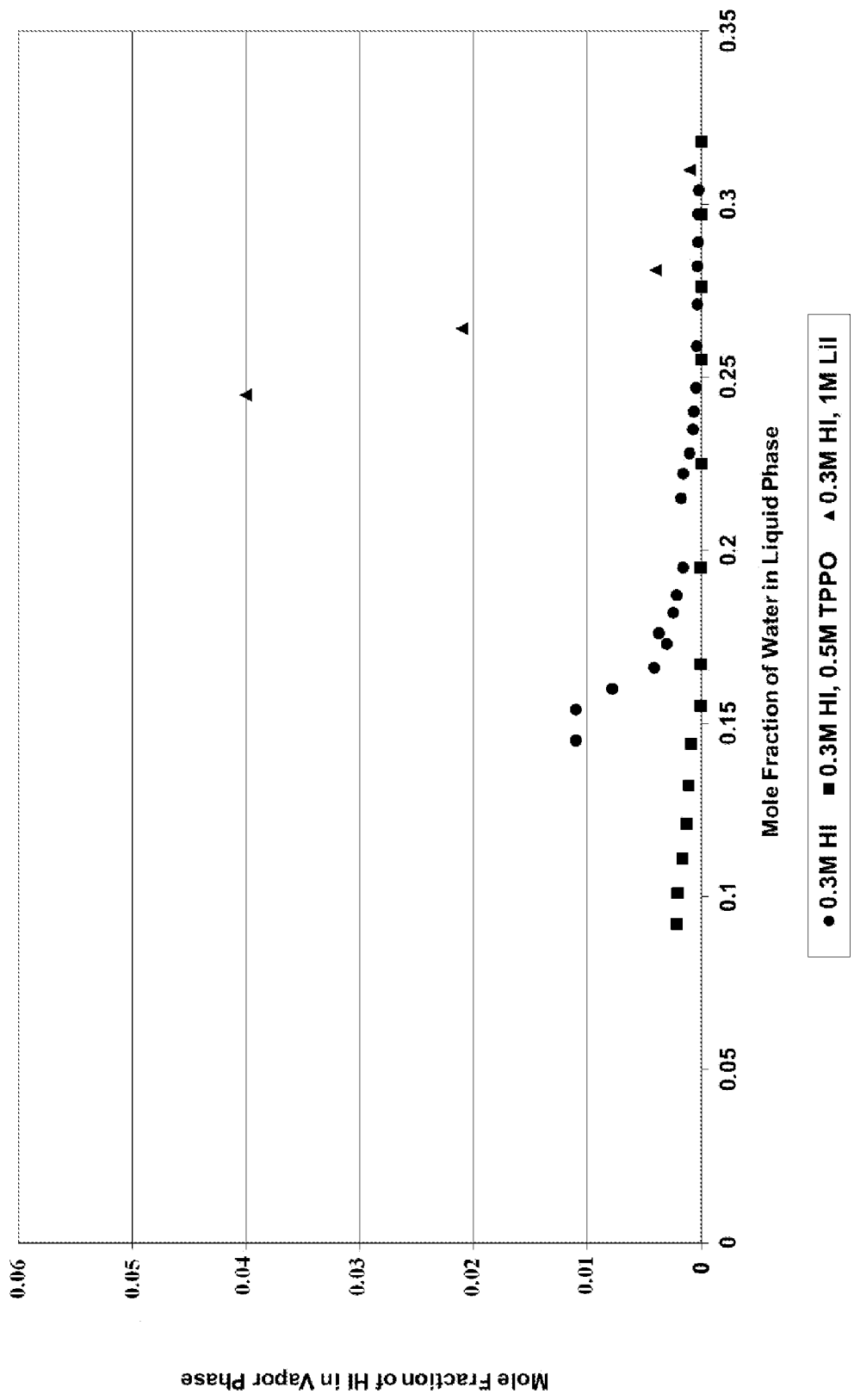
FIG. 4 depicts the results of investigations into the impact of triphenylphosphine oxide and lithium iodide on the VLE of hydrogen iodide in aqueous acetic acid.

FIG. 4 shows that the presence of LM lithium iodide increases the volatility of hydrogen iodide whereas 0.5M triphenylphosphine oxide reduces the volatility of hydrogen iodide.

Figure 5:
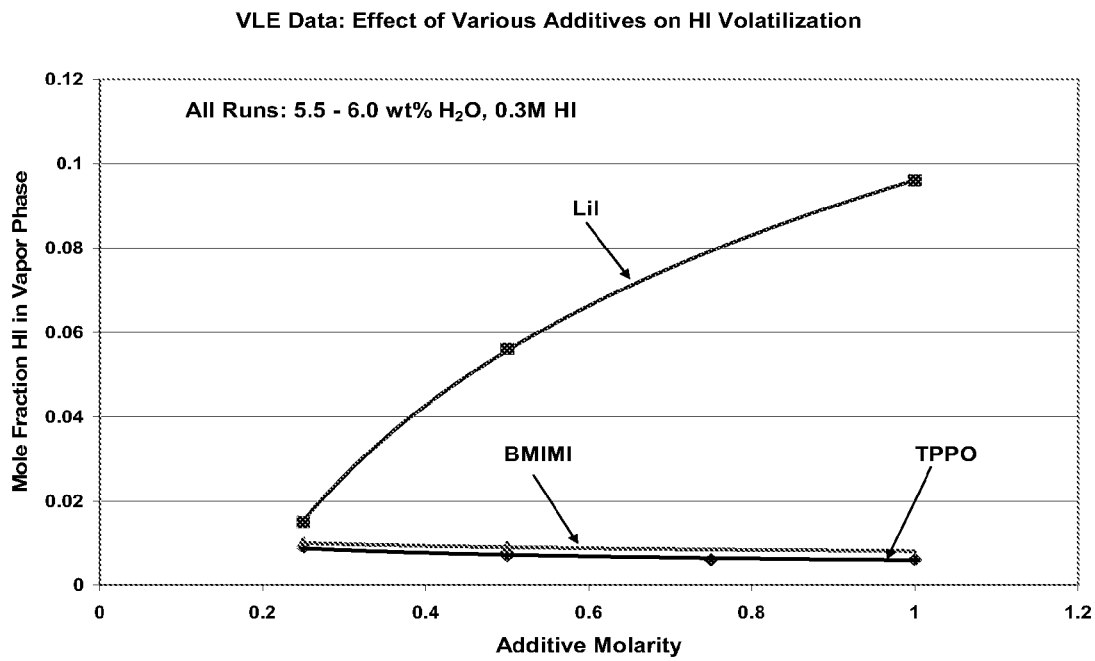
FIG. 5 depicts the results of investigations into the impact of triphenylphosphine oxide, lithium iodide, and 1-butyl, 3-methylimidazolium iodide on the VLE of hydrogen iodide in acetic acid comprising 5.5-6 wt. % of water.
Figure 6:
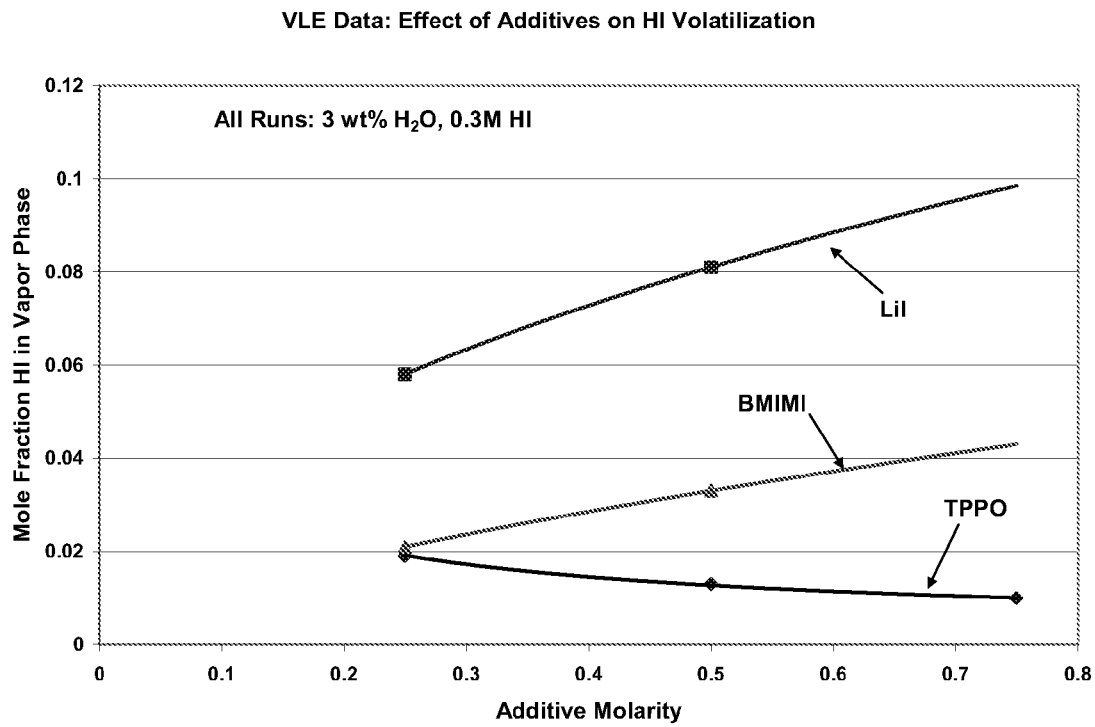
FIG. 6 depicts the results of investigations into the impact of triphenylphosphine oxide, lithium iodide, and 1-butyl, 3-methylimidazolium iodide on the VLE of hydrogen iodide in acetic acid comprising 3 wt. % of water.

FIGS. 5 and 6 show the effect of lithium iodide (LiI), triphenylphosphine oxide (TPPO), and 1-butyl, 4-methylimidazolium iodide (BMIMI) on the volatility of hydrogen iodide at a water concentration of 5.5-6 wt. % and 3 wt. %, respectively.

The following investigations and examples are intended to be illustrative only, and are not intended to be, nor should they be construed as, limiting the scope of the present invention in any way.

EXAMPLES

1. Vapor-Liquid-Equilibrium (VLE) Investigations

The investigations were carried out in two different types of recirculation apparatus as shown schematically in FIGS. 2 and 3. Apparatus 1 was used for the experiments described in Examples 1 to 3, the results of which are depicted in FIG. 4. Apparatus 2 was used for the experiments described in Examples 4 to 21 the results of which are compiled in Tables 2 and 3 and depicted in FIGS. 5 and 6.

General Procedure A:

In the case of Apparatus 1, a 1 l flask was charged with a total of 500 grams of appropriate amounts of acetic acid, water, hydrogen iodide (HI) and optionally triphenylphosphine oxide (TPPO) or lithium iodide (LiI). The stirred solution was brought to reflux. After one hour of condensation/liquid return, a 10-20 gram sample of vapor condensate was collected. A 0.2 ml sample was also removed from the flask for analysis. A volume of acetic acid equivalent to the volume of the removed condensate sample was added to the flask and the solution was allowed to reflux for about 30 minutes before the sampling procedure was repeated and a further aliquot of acetic acid was added. This procedure was repeated until the concentration of water in the flask had decreased to the desired level.

General Procedure B:

In the case of Apparatus 2, the 150 grams of a mixture of appropriate amounts of acetic acid, water, hydrogen iodide (HI), lithium iodide (LiI), triphenylphosphine oxide (TPPO), 1-butyl, 4-methylimidazolium iodide (BMIMI), 1-butyl, 2,3-dimethylimidazolium iodide (BDMIMI), and 1-dodecycl, 3-methylimidazolium iodide (DOMIMI) were charged to the flask under atmospheric pressure and slight $N_2$ purge. The mixture was refluxed for about 1 hour during which period the condensate was recirculated to the flask. Thereafter, a sample of the condensate and a sample of the mixture were withdrawn for analysis, and the experiment was terminated.

Water concentration in condensed vapor samples and in pot liquid samples was measured by Karl Fischer titration. Iodide concentration in those experiments containing iodide was determined either by titration with silver nitrate or by a visible spectro-photometric method in which iodide is first rapidly oxidized to iodine by hydrogen peroxide and then quantified by the iodine absorption band at 475 nm.

Validation of VLE Apparatus 1 and VLE Apparatus 2:

As those skilled in the art will appreciate, it is critical that the apparatus operate in adiabatic fashion in which only one equilibrium stage is present and in which there is no enrichment of the vapor in the more volatile component by partial condensation. As such, the suitability of Apparatus 1 and Apparatus 2 was validated before use by determining the water concentration in the vapor condensate at flask water concentrations of 5, 10 and 20 wt. % in acetic acid. The extent of enrichment of the more volatile water in the vapor phase upon heating the samples to reflux and upon analyzing a condensed vapor sample and a liquid pot sample, matched well with previous literature values as shown in Table 1 where all values are expressed as mole fractions.

TABLE 1

Validation of VLE Apparatus 1 and VLE Apparatus 2 by comparison with prior art data

| $H_2O$, Liq | $H_2O^1$, Vap | $H_2O^2$, Vap | $H_2O^3$, Vap | $H_2O^4$, Vap |
|---|---|---|---|---|
| 0.15 | 0.26 | 0.23 | 0.26 | 0.23 |
| 0.28 | 0.41 | 0.41 | 0.41 | 0.4 |
| 0.47 | 0.61 | 0.6 | 0.61 | |

[1] = Apparatus 1
[2] = Apparatus 2
[3] = EP 0 506 240
[4] = Brown et al., Aust. J. Sci. Res. Series A 3, 306 (1950)

Example 1

General Procedure A 500 grams of a solution composed of 12 wt. % water, 3.8 wt. % hydrogen iodide and 84.2 wt. % acetic acid was charged to the Apparatus 1 flask. As described above, the water concentration in the flask was decreased from 12 wt. % to about 5 wt. % in increments of about 0.5 wt. % by removal of aliquots of condensed vapor sample and replenishing the flask with a similar volume of acetic acid. The water and iodide concentration of the condensed vapor sample and of the pot solution were determined after each removal, thus allowing the mole fractions of all components to be calculated. The results are depicted in FIG. 4 which shows a rapid increase in hydrogen iodide in the vapor phase as water concentration in the pot is lowered.

Example 2

500 grams of a solution composed of 12 wt. % water, 3.8 wt. % hydrogen iodide, 13.0 wt. % triphenylphosphine oxide and 71.2 wt. % acetic acid was charged to Apparatus 1 and an experiment conducted as described in Example 1. The results are depicted in FIG. 4 which shows that in the presence of triphenylphosphine oxide, there is very little hydrogen iodide in the vapor phase compared to Example 1.

Example 3

500 grams of a solution composed of 12 wt. % water, 3.8 wt. % hydrogen iodide, 13.0 wt. % lithium iodide and 71.2 wt. % acetic acid was charged to Apparatus 1 and an experiment conducted as described in Example 1. The results are depicted in FIG. 4 which shows that in the presence of lithium iodide, there is a rapid increase in hydrogen iodide in the vapor phase, even when there remains a high mole fraction of water in the liquid phase.

Example 4

General Procedure B 150 grams of a solution composed of 5.8 wt. % water, 3.7 wt. % hydrogen iodide and 90.5 wt. % acetic acid was charged to the Apparatus 2 flask. After one hour of refluxing, a condensed vapor sample and a pot sample were removed for analysis. The results are compiled in Table 2.

Example 5

Example 4 was repeated with an initial solution composed of 5.8 wt. % water, 3.7 wt. % hydrogen iodide, 6.7 wt. %

1-butyl, 4-methylimidazolium iodide and 83.8 wt. % acetic acid. The results are compiled in Table 2 and depicted in FIG. 5.

Example 6

Example 4 was repeated with an initial solution composed of 5.8 wt. % water, 3.7 wt. % hydrogen iodide, 13.3 wt. % 1-butyl, 4-methylimidazolium iodide and 77.2 wt. % acetic acid. The results are compiled in Table 2 and depicted in FIG. 5.

Example 7

Example 4 was repeated with an initial solution composed of 6.0 wt. % water, 3.7 wt. % hydrogen iodide, 6.7 wt. % triphenylphosphine oxide and 83.6 wt. % acetic acid. The results are compiled in Table 2 and depicted in FIG. 5.

Example 8

Example 4 was repeated with an initial solution composed of 6.0 wt. % water, 3.7 wt. % hydrogen iodide, 13.3 wt. % triphenylphosphine oxide and 77.0 wt. % acetic acid. The results are compiled in Table 2 and depicted in FIG. 5.

Example 9

Example 4 was repeated with an initial solution composed of 6.0 wt. % water, 3.9 wt. % hydrogen iodide, 3.3 wt. % lithium iodide and 86.8 wt. % acetic acid. The results are compiled in Table 2 and depicted in FIG. 5.

Example 10

Example 4 was repeated with an initial solution composed of 5.5 wt. % water, 3.8 wt. % hydrogen iodide, 6.6 wt. % lithium iodide and 84.1 wt. % acetic acid. The results are compiled in Table 2 and depicted in FIG. 5.

TABLE 2

Effect of lithium iodide (LiI), triphenylphosphine oxide (TPPO), and 1-butyl, 4-methylimidazolium iodide (BMIMI) on volatilization of hydrogen iodide (HI) from acetic acid containing 5.5-6 wt. % of water

| Ex. | Additive | Additive Concentration [M] | Mol Fraction of HI in Condensed Vapor |
|---|---|---|---|
| 04 | None (control) | —/— | 0.012 |
| 05 | BMIMI | 0.25 | 0.01 |
| 06 |  | 0.5 | 0.009 |
| 07 | TPPO | 0.25 | 0.009 |
| 08 |  | 0.5 | 0.007 |
| 09 | LiI | 0.25 | 0.015 |
| 10 |  | 0.5 | 0.058 |
| 11 |  | 1.0 | 0.096 |

Example 11

Example 4 was repeated with an initial solution composed of 2.9 wt. % water, 3.7 wt. % hydrogen iodide and 93.4 wt. % acetic acid. The results are compiled in Table 3.

Example 12

Example 4 was repeated with an initial solution composed of 2.9 wt. % water, 3.7 wt. % hydrogen iodide, 6.7 wt. % 1-butyl, 4-methylimidazolium iodide and 86.7 wt. % acetic acid. The results are compiled in Table 3 and depicted in FIG. 6.

Example 13

Example 4 was repeated with an initial solution composed of 2.9 wt. % water, 3.7 wt. % hydrogen iodide, 13.3 wt. % 1-butyl, 4-methylimidazolium iodide and 80.1 wt. % acetic acid. The results are compiled in Table 3 and depicted in FIG. 6.

Example 14

Example 4 was repeated with an initial solution composed of 2.9 wt. % water, 3.7 wt. % hydrogen iodide, 7.0 wt. % 1-butyl, 2,3-dimethylimidazolium iodide and 86.4 wt. % acetic acid. The results are compiled in Table 3 and depicted in FIG. 6.

Example 15

Example 4 was repeated with an initial solution composed of 2.9 wt. % water, 3.7 wt. % hydrogen iodide, 9.5 wt. % 1-dodecycl, 3-methylimidazolium iodide and 83.9 wt. % acetic acid. The results are compiled in Table 3.

Example 16

Example 4 was repeated with an initial solution composed of 2.9 wt. % water, 3.7 wt. % hydrogen iodide, 6.7 wt. % triphenylphosphine oxide, 6.7 wt. % 1-butyl, 4-methylimidazolium iodide and 80.0 wt. % acetic acid. The results are compiled in Table 3 and depicted in FIG. 6.

Example 17

Example 4 was repeated with an initial solution composed of 2.9 wt. % water, 3.7 wt. % hydrogen iodide, 6.7 wt. % 1-butyl, 4-methylimidazolium iodide, 3.3 wt. % lithium iodide and 83.4 wt. % acetic acid. The results are compiled in Table 3 and depicted in FIG. 6.

Example 18

Example 4 was repeated with an initial solution composed of 3.1 wt. % water, 3.9 wt. % hydrogen iodide, 6.6 wt. % triphenylphosphine oxide and 86.4 wt. % acetic acid. The results are compiled in Table 3 and depicted in FIG. 6.

Example 19

Example 4 was repeated with an initial solution composed of 2.9 wt. % water, 3.7 wt. % hydrogen iodide, 13.3 wt. % triphenylphosphine oxide and 80.1 wt. % acetic acid. The results are compiled in Table 3 and depicted in FIG. 6.

Example 20

Example 4 was repeated with an initial solution composed of 2.9 wt. % water, 3.7 wt. % hydrogen iodide, 3.3 wt. % lithium iodide and 90.1 wt. % acetic acid. The results are compiled in Table 3 and depicted in FIG. 6.

Example 21

Example 4 was repeated with an initial solution composed of 2.9 wt. % water, 3.7 wt. % hydrogen iodide, 6.6 wt. % lithium iodide and 86.8 wt. % acetic acid. The results are compiled in Table 3 and depicted in FIG. 6.

TABLE 3

Effect of lithium iodide (LiI), triphenylphosphine oxide (TPPO), 1-butyl, 4-methylimidazolium iodide (BMIMI), 1-butyl, 2,3-dimethylimidazolium iodide (BDMIMI), and 1-dodecycl, 3-methylimidazolium iodide (DOMIMI) on volatilization of hydrogen iodide (HI) from acetic acid containing 3 wt. % of water

| Ex. | Additive | Additive Concentration [M] | Mol Fraction of HI in Condensed Vapor |
|---|---|---|---|
| 11 | None (control) | —/— | 0.048 |
| 12 | BMIMI | 0.25 | 0.021 |
| 13 | | 0.5 | 0.033 |
| 14 | BDMIMI | 0.25 | 0.023 |
| 15 | DOMIMI | 0.25 | 0.041 |
| 16 | TPPO + BMIMI | 0.25 + 0.25 | 0.017 |
| 17 | LiI + BMIMI | 0.25 + 0.25 | 0.049 |
| 18 | TPPO | 0.25 | 0.019 |
| 19 | | 0.5 | 0.013 |
| 20 | LiI | 0.25 | 0.058 |
| 21 | | 0.5 | 0.081 |

In particular, Table 2 and FIG. 5 illustrate that the effect of the alkylimidazolium iodide (BMIMI) on the suppression of hydrogen iodide is similar to that of triphenylphosphine oxide (TPPO). In contrast, lithium iodide increases the volatility of hydrogen iodide in a concentration dependent manner, i.e., an increase of almost an order of magnitude is observed when the concentration of lithium iodide is increased from 0.25 M to 1.0 M.

We claim:

1. A process for producing acetic acid which comprises:
   (a) carbonylating methanol in the presence of a catalyst in a reaction zone to obtain a reaction zone to obtain a reaction mixture (A) comprising the acetic acid, hydrogen iodide, methyl iodide, water and the catalyst;
   (b) withdrawing at least a part of the reaction mixture (A) from the reaction zone;
   (c) introducing the withdrawn part of the reaction mixture (A) into a flash zone;
   (d) contacting the withdrawn part of the reaction mixture (A) in the flash zone with an alkylimidazolium iodide to form a secondary mixture (B);
   (e) separating the secondary mixture (B) in the flash zone to obtain a vapor stream ($B_V$) comprising acetic acid, water and methyl iodide, and a liquid stream ($B_L$) comprising the catalyst, the alkylimidazolium iodide and hydrogen iodide; and
   (f) recycling the liquid stream ($B_L$) to the reaction zone;
   wherein the reaction mixture (A) is brought into contact with the alkylimidazolium iodide in the flash zone
   1) by introducing to the flash zone separately from the withdrawn reaction mixture (A) an extraneous alkylimidazolium iodide; or
   2) by introducing to the flash zone separately from the withdrawn reaction mixture (A) an alkylimidazole and forming the alkylimidazolium iodide in situ by reacting the alkylimidazole with the hydrogen iodide and/or the methyl iodide.

2. The process of claim 1, wherein the withdrawn reaction mixture (A) is brought into contact with the alkylimidazolium iodide in the flash zone by introducing the extraneous alkylimidazolium iodide to the flash zone.

3. The process of claim 2, wherein the extraneous alkylimidazolium iodide is a compound of formula (I)

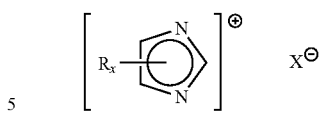

wherein x is 1, 2, 3 or 4, each R independently is $C_1$-$C_6$-alkyl, and $X^-$ is an iodine anion.

4. The process of claim 2, wherein the extraneous alkylimidazolium iodide is a compound of formula (Ia)

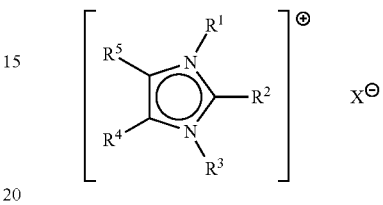

wherein
   $R^1$ is hydrogen or $C_1$-$C_6$-alkyl;
   $R^2$, $R^3$, $R^4$ and $R^5$, each independently, is hydrogen or $C_1$-$C_2$-alkyl; and
   $X^-$ is an iodine anion;
   and wherein at least one of $R^1$, $R^2$, $R^3$, $R^4$ and $R^5$ is different from hydrogen, and at least one of $R^1$, $R^2$, $R^3$, $R^4$ and $R^5$ denotes hydrogen.

5. The process of claim 4, wherein the extraneous alkylimidazolium iodide is a hydrogen iodide or $C_1$-$C_6$-alkyl iodide salt of at least one alkylimidazole selected from the group consisting of 1-methylimidazole, 1-ethylimidazole, 1-propylimidazole, 1-isopropylimidazole, 1-(1-butyl)imidazole, 1-(2-butyl)imidazole, 1-isobutylimidazole, 1-tert-butylimidazole, 3-methylimidazole, 3-ethylimidazole, 4-methylimidazole, 4-ethylimidazole, 1,4-dimethylimidazole, 1,4-diethylimidazole, 1-ethyl-4-methylimidazole, 4-ethyl-1-methylimidazole, 2-methyl-1-propylimidazole, 4-methyl-1-propylimidazole, 5-methyl-1-propylimidazole, 2,4-dimethyl-1-propylimidazole, 2,5-dimethyl-1-propylimidazole, 1-isopropyl-2-methylimidazole, 1-isopropyl-4-methylimidazole, 1-isopropyl-5-methylimidazole, 2,4-dimethyl-1-isopropylimidazole, 2,5-dimethyl-1-isopropylimidazole, 1-(1-butyl)-2-methylimidazole, 1-(1-butyl)-4-methylimidazole, 1-(1-butyl)-5-methylimidazole, 1-(1-butyl)-2,4-dimethylimidazole, 1-(1-butyl)-2,5-dimethylimidazole, 1-(2-butyl)-2-methylimidazole, 1-(2-butyl)-4-methylimidazole, 1-(2-butyl)-5-methylimidazole, 1-(2-butyl)-2,4-dimethylimidazole, 1-(2-butyl)-2,5-dimethylimidazole, 1-isobutyl-2-methylimidazole, 1-isobutyl-4-methylimidazole, 1-isobutyl-5-methylimidazole, 1-isobutyl-2,4-dimethylimidazole, 1-isobutyl-2,5-dimethylimidazole, 1-tert-butyl-2-methylimidazole, 1-tert-butyl-4-methylimidazole, 1-tert-butyl-5-methylimidazole, 1-tert-butyl-2,4-dimethylimidazole, and 1-tert-butyl-2,5-dimethylimidazole.

6. The process of claim 2, wherein the extraneous alkylimidazolium iodide is introduced to the flash zone separately and independently from any recycle stream which is recovered downstream of the flash zone.

7. The process of claim 2, wherein the extraneous alkylimidazolium iodide is introduced to the flash zone by adding the extraneous alkylimidazolium iodide to a recycle stream recovered downstream of the flash zone and introducing the recycle stream comprising the added alkylimidazolium iodide to the flash zone.

8. The process of claim 1, wherein the withdrawn reaction mixture (A) is brought into contact with the alkylimidazolium iodide in the flash zone by introducing the alkylimidazole to the flash zone and forming the alkylimidazolium iodide in situ.

9. The process of claim 8, wherein the alkylimidazole is a compound of formula (II)

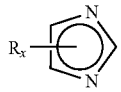

wherein x is 1, 2 or 3, and each R independently is $C_1$-$C_6$-alkyl.

10. The process of claim 8, wherein the alkylimidazole is a compound of formula (IIa)

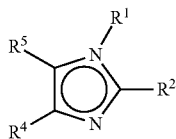

wherein
$R^1$ is hydrogen or $C_1$-$C_6$-alkyl;
$R^2$, $R^4$ and $R^5$, each independently, is hydrogen, or $C_1$-$C_2$-alkyl;
and wherein at least one of $R^1$, $R^2$, $R^4$ and $R^5$ is different from hydrogen, and at least one of $R^1$, $R^2$, $R^4$ and $R^5$ is hydrogen.

11. The process of claim 10, wherein the alkylimidazole is 1-methylimidazole, 1-ethylimidazole, 1-propylimidazole, 1-isopropylimidazole, 1-(1-butyl)imidazole, 1-(2-butyl)imidazole, 1-isobutylimidazole, 1-tert-butylimidazole, 3-methylimidazole, 3-ethylimidazole, 4-methylimidazole, 4-ethylimidazole, 1,4-dimethylimidazole, 1,4-diethylimidazole, 1-ethyl-4-methylimidazole, 4-ethyl-1-methylimidazole, 2-methyl-1-propylimidazole, 4-methyl-1-propylimidazole, 5-methyl-1-propylimidazole, 2,4-dimethyl-1-propylimidazole, 2,5-dimethyl-1-propylimidazole, 1-isopropyl-2-methylimidazole, 1-isopropyl-4-methylimidazole, 1-isopropyl-5-methylimidazole, 2,4-dimethyl-1-isopropylimidazole, 2,5-dimethyl-1-isopropylimidazole, 1-(1-butyl)-2-methylimidazole, 1-(1-butyl)-4-methylimidazole, 1-(1-butyl)-5-methylimidazole, 1-(1-butyl)-2,4-dimethylimidazole, 1-(1-butyl)-2,5-dimethylimidazole, 1-(2-butyl)-2-methylimidazole, 1-(2-butyl)-4-methylimidazole, 1-(2-butyl)-5-methylimidazole, 1-(2-butyl)-2,4-dimethylimidazole, 1-(2-butyl)-2,5-dimethylimidazole, 1-isobutyl-2-methylimidazole, 1-isobutyl-4-methylimidazole, 1-isobutyl-5-methylimidazole, 1-isobutyl-2,4-dimethylimidazole, 1-isobutyl-2,5-dimethylimidazole, 1-tert-butyl-2-methylimidazole, 1-tert-butyl-4-methylimidazole, 1-tert-butyl-5-methylimidazole, 1-tert-butyl-2,4-dimethylimidazole, and 1-tert-butyl-2,5-dimethylimidazole.

12. The process of claim 8, wherein the alkylimidazole is introduced to the flash zone separately and independently from any recycle stream which is recovered downstream of the flash zone.

13. The process of claim 8, wherein the alkylimidazole is introduced to the flash zone by adding the alkylimidazole to a recycle stream recovered downstream of the flash zone and introducing the recycle stream comprising the added alkylimidazole or, where applicable, the corresponding alkylimidazolium iodide, to the flash zone.

14. The process of claim 1, wherein the reaction mixture (A) does not comprise an alkylimidazolium iodide other than the alkylimidazolium iodide of the secondary mixture (B) which has been recycled to the reaction zone.

15. The process of claim 1, wherein the catalyst is a rhodium catalyst.

16. The process of claim 1, wherein the reaction mixture (A) comprises at least one catalyst stabilizer selected from the group consisting of phosphine oxides and iodides of a metal of Group 1 or 2 of the Periodic Table of the Elements.

17. The process of claim 16, wherein the stabilizer is triphenylphosphine oxide and/or lithium iodide.

18. The process of claim 1, wherein the reaction mixture (A) does not comprise a catalyst stabilizer selected from the group consisting of phosphine oxides and iodides of metals of Group 1 or 2 of the Periodic Table of the Elements.

19. The process of claim 1, wherein the reaction mixture (A) comprises water in a concentration of from about 0.2% to about 10% by weight.

* * * * *